United States Patent [19]

Melvin, II et al.

[11] Patent Number: 5,861,548
[45] Date of Patent: Jan. 19, 1999

[54] APPARATUS AND METHOD UTILIZING SIGNAL MODULATION DETECTION FOR ANALYZING THE INTERNAL PRESSURE OF CONTAINERS

[75] Inventors: Robert G. Melvin, II, Sandwich; Robert J. Ryan, Dennis, both of Mass.

[73] Assignee: Benthos, Inc., North Falmouth, Mass.

[21] Appl. No.: 71,787

[22] Filed: May 1, 1998

Related U.S. Application Data

[60] Provisional application No. 60/047,611 May 23, 1997.

[51] Int. Cl.⁶ .............................. G01M 3/00; G01L 9/10; G01N 29/04
[52] U.S. Cl. .................................. 73/52; 73/49.3; 73/587; 73/598
[58] Field of Search ............................ 73/52, 49.3, 45.4, 73/587, 579, 592, 602

[56] References Cited

U.S. PATENT DOCUMENTS

| | | | |
|---|---|---|---|
| 3,802,252 | 4/1974 | Hayward et al. | 73/52 |
| 4,187,718 | 2/1980 | Shibasaki | 73/52 |
| 4,212,205 | 7/1980 | West et al. | 73/579 |
| 4,213,329 | 7/1980 | Raymond et al. | 73/52 |
| 4,399,514 | 8/1983 | Hamasaki et al. | 364/558 |
| 4,406,157 | 9/1983 | Miyahara et al. | 73/52 |
| 4,821,573 | 4/1989 | Nagata et al. | 73/597 |
| 4,869,097 | 9/1989 | Tittmann et al. | 73/52 |
| 5,351,527 | 10/1994 | Blackburn et al. | 73/52 |
| 5,353,631 | 10/1994 | Woringer et al. | 73/52 |
| 5,369,600 | 11/1994 | Ito et al. | 364/556 |
| 5,591,900 | 1/1997 | Bronowocki et al. | 73/52 |
| 5,608,164 | 3/1997 | MacLauchlan | 73/599 |
| 5,675,074 | 10/1997 | Mclvin, II | 73/52 |

Primary Examiner—Hezron Williams
Assistant Examiner—J. David Wiggins
Attorney, Agent, or Firm—Francis J. Caufield

[57] ABSTRACT

A method for analyzing the internal pressure of a closed container includes inducing vibration in a surface of the container; detecting sound resulting from the vibration; deriving information representing the detecting sound; and determining whether this information corresponds to a predetermined spectral frequency condition and a predetermined spectral amplitude condition. To ensure that the test results are not affected by modulating distortion which may be present in the information, the information is tested for the presence of a modulating distortion, and if so processed to compensate for the effects of this modulating distortion, prior to being tested against the predetermined spectral conditions. Alternatively or in addition, one or both of the upper and lower amplitude limits which define the spectral amplitude condition may be reset periodically to allow for slow changes in manufacturing conditions by accumulating amplitude data from a plurality of containers judged to have an acceptable internal pressure, analyzing this amplitude data to derive an average value and a deviation therefrom, and resetting one or both of the amplitude limits in dependence upon the derived average value and deviation.

45 Claims, 9 Drawing Sheets

APPARATUS AND METHOD UTILIZING SIGNAL MODULATION DETECTION FOR ANALYZING THE INTERNAL PRESSURE OF CONTAINERS

CROSS REFERENCE TO RELATED APPLICATION AND PATENT

This application claims priority from commonly owned U.S. Provisional patent application Ser. No. 60/047,611 filed on May 23, 1997. Attention is also directed to commonly owned and related U.S. Pat. No. 5,675,074 issued Oct. 7, 1997 to Robert G. Melvin, II; the entire disclosure of this patent is herein incorporated by reference.

BACKGROUND OF THE INVENTION

This invention generally relates to apparatus and methods for characterizing the internal pressure of closed containers and more particularly to apparatus and methods that detect and compensate for signal distortions in performing such analyses.

Food, beverage, and drug containers, for example, are often sealed under vacuum (e.g., coffee) or internal pressurization (e.g., beer). If biological contamination or seal failure occurs, the product quality may be significantly degraded and may be dangerous to consumers. Accordingly, manufacturers test the internal pressure/vacuum of containers before shipment to identify and remove defective containers.

Two non-intrusive testing techniques are shown in Hayward, U.S. Pat. No. 3,802,252 and Woringer, U.S. Pat. No. 5,353,631, both of which are assigned to Benthos™, Inc., and incorporated herein by reference. Systems of the type described in the foregoing patents have been sold under the name TapTone™. In such systems, a conductive surface of a closed container is vibrated without contacting it. This is accomplished using a pulsed magnetic field, and the resulting sound is analyzed to determine the pressure in the container. A microphone senses the resulting acoustic energy and converts it into an electrical signal. In the Hayward scheme, analog electronics are used to determine whether the signal has a detectable level of energy within a pre-tuned frequency band. If a signal is detected within the band, it is inferred that the can is good. In the Woringer scheme, a similar test is performed using digital signal processing (DSP) electronics and software.

Because closed containers are complex vibratory systems which often exhibit nonlinear effects, it is not uncommon to find in the use of such systems that the acoustic return signals have been modulated by vibratory modes of the container other than the fundamental mode typically used to predict internal pressure. When such distortions are present, the information contained in the acoustic signal has been corrupted by misleading information that can lead to false rejections of containers.

Consequently, it is a primary object of the present invention to provide apparatus and methods for detecting and compensating for the presence of extraneous signal modulation in acoustic signatures used to characterize the internal pressure of containers.

It is another object of the present invention to provide apparatus and methodology for dynamically changing the process control limits for judging internal pressure as a function of slowly varying changes in the upstream container filling process to optimize throughput without permitting the passage of reject containers.

Other objects of the invention and will in part appear hereinafter and will in part be obvious when the following detailed description is read in connection with the drawings.

SUMMARY OF THE INVENTION

In general, in one aspect, the invention features apparatus and methodology including inducing vibration in a surface of a closed container, detecting sound resulting from the vibration, and deriving information representing the detected sound. The method further includes determining whether the sound contains modulation which must be compensated for before subsequent use of the information for predicting container internal pressure.

Implementations of the invention may include one or more of the following. The surface may be at least partially conductive, and inducing may include imposing a magnetic field on the surface. Determining may include comparing the information to the predetermined spectral frequency and spectral amplitude conditions which may correspond to ranges of acceptable values. The information may include digital data and may represent a frequency spectrum peak. The detected sound may include other modulated signals which may need to be removed to determine a single frequency spectrum peak. The predetermined spectral frequency and spectral amplitude conditions may define a good or a bad container region, and determining may include comparing the frequency and the amplitude of a spectral frequency peak to the good or bad container region. The detected sound may be used to determine whether the closed container contains a pressure level within a predetermined range of pressure levels.

In general, in another aspect, the invention features a method including inducing vibration in a surface of a closed container by imposing a magnetic field on the surface, detecting sound resulting from the vibration, and deriving information representing the detected sound. The method further includes determining whether the data contains a modulated signal and, if so, to be able to remove the modulation from the signal or compensate for it so information contained in the modulated signal can be used to correctly determine if the signal corresponds to a predetermined frequency condition and a predetermined amplitude condition. The predetermined frequency condition corresponds to a range of acceptable frequencies, and the predetermined amplitude condition corresponds to a minimum or a maximum amplitude threshold. Determining includes comparing the data to the range of acceptable frequencies and to the amplitude thresholds.

In general, in another aspect, the invention features a method of operating a manufacturing line, including passing closed containers through a container inspection system and, at the container inspection system, inducing vibration in a surface of each of the closed containers, detecting sound resulting from the vibration, and deriving information representing the detected sound. The method further includes determining whether the information contains a modulation component and removing or compensating for that component.

Implementations of the invention may include one or more of the following. Inducing may include imposing a magnetic field on the surface of each of the closed containers, and determining may include comparing the information to the predetermined spectral frequency and spectral amplitude conditions. The information may include a modulation component which may need to be removed or compensated for. The information may represent a spectral frequency peak.

The predetermined spectral frequency and spectral amplitude conditions may define a good container region, and determining may include comparing the frequency and the amplitude of a spectral frequency peak to the good container region. Containers may be rejected or accepted based on the results of the determining step. For instance, containers with associated frequency peaks that are outside the good container region may be rejected, while containers with associated frequency peaks that are within the good container region are accepted. Containers with associated spectral frequency peaks that are outside a range of acceptable frequencies may be rejected as well as containers with associated spectral frequency peaks that are within a range of acceptable frequencies but which have amplitudes below a minimum amplitude threshold or above a maximum amplitude threshold. Rejected containers may contain a pressure level below a predetermined range of acceptable pressure levels.

The predetermined spectral frequency condition and the predetermined spectral amplitude condition may define a bad container region, and determining may include comparing the frequency and the amplitude of a spectral frequency peak to the bad container region. Containers with associated spectral frequency peaks that are within the bad container region may be rejected while containers with associated spectral frequency peaks that are outside the bad container region may be accepted.

In general, in another aspect, the invention features a container inspection system for use with a closed container including an electromagnetic field source for inducing vibration in a surface of the container. The surface is at least partially conductive. The inspection system also includes an acoustic transducer for measuring reactant sound produced by the vibration, and a controller electrically connected to the acoustic transducer, for detecting a frequency peak within the reactant sound and for comparing the frequency peak to a good container region. The good container region is defined by a predetermined frequency condition and a predetermined amplitude condition.

Implementations of the invention may include one or more of the following. The container inspection system may further include a rejecting station for rejecting containers with associated spectral frequency peaks outside the good container region. The predetermined frequency condition may include a range of frequencies, and the predetermined amplitude condition may include a minimum amplitude threshold and a maximum amplitude threshold. The rejecting station may reject containers with associated frequency peaks outside the predetermined range of acceptable frequencies and containers with associated frequency peaks within the predetermined range of acceptable frequencies and having an amplitude below the minimum amplitude threshold or above the maximum amplitude threshold. The controller may include a digital signal processor for receiving and performing a fast Fourier transform (FFT) on electrical signals from the acoustic detection device to provide the signal spectral characteristics. The acoustic transducer may include a microphone, and the electromagnetic field source may include a conductive coil. The container inspection system may further include a conveyor belt for carrying the containers through the inspection system and a rotary position encoder connected to a drive shaft of the conveyor belt and to the controller. The detector may be used to detect changes in the pressure level contained by the container.

In general, in another aspect, the invention features a container inspection system for use with a closed container including an electromagnetic field source for inducing vibration in a surface of the container where at least a portion of the surface is at least partially conductive. The container inspection system further includes an acoustic detection device for detecting reactant sound produced by the container in response to the imposition of the magnetic field, and a controller electrically connected to the acoustic detection device, for detecting a spectral frequency peak within the reactant sound and for comparing the frequency peak to a bad container region. Examples are sound generated from a metal cap on a glass bottle and the metal surface of a beverage can. The bad container region is defined by a predetermined frequency condition and a predetermined amplitude condition.

Implementation of the invention may include one or more of the following. The container inspection system may further include a rejecting station for rejecting containers with associated spectral frequency peaks within the bad container region. The predetermined frequency condition may include a range of frequencies, and the predetermined amplitude condition may include a minimum amplitude threshold and a maximum amplitude threshold. The controller may include a digital signal processor for receiving and performing a fast Fourier transform on electrical signals from the acoustic transducer.

In general, in another aspect, the invention features an apparatus for analyzing internal pressure of a closed container including a conductive coil for inducing vibration in a surface of the container where the surface is at least partially conductive. The apparatus also includes circuitry for deriving a frequency versus amplitude spectrum of the vibration, digital storage for holding the spectrum and for holding data sufficient to analyze the internal pressure based on the spectrum, and a processor for analyzing the internal pressure based on the spectrum and the data.

Implementations of the invention may include one or more of the following. The processor may include means for analyzing the internal pressure based on the frequency and amplitude of a peak of the spectrum.

In general, in another aspect, the invention features an apparatus for analyzing internal pressure of a series of closed containers moving along a manufacturing line including a conductive coil for inducing vibration in a surface of the container where the surface is at least partially conductive. The apparatus further includes an analyzer for deriving a frequency versus amplitude spectrum of the vibration, digital storage for holding the spectrum and data sufficient to analyze the internal pressure based on the spectrum, and a processor for generating the data. The processor including means for energizing the coil and controlling the analyzer to generate frequency versus amplitude spectra for vibrations of a series of test containers having different, known internal pressures, and means for deriving the data from the spectra.

In general, in another aspect, the invention features an apparatus for analyzing the internal pressure of a closed container including a conductive coil for inducing vibration in a surface of the container where the surface is at least partially conductive and a sensor for detecting the vibration. The apparatus further includes storage for holding time domain data corresponding to the vibration, circuitry and associated software for deriving a frequency versus amplitude spectrum from the time domain data, and a display for showing a two-dimensional graphic image of the spectrum.

Rapid, accurate determinations of the internal pressure/vacuum of a variety of containers, including cans, pop top bottles, and vacuum packed foil bags, are made by analyzing the acoustic response of a closed container using both frequency and minimum and maximum amplitudes of the acoustic spectral content. Improperly pressurized or vacuumed containers are detected because the amplitude of a frequency peak in the container's reactant sound is too high or too low when the frequency of the peak is within a selected frequency range.

A rotary position (shaft) encoder provides a controller with the current speed of the manufacturing line. Using both the shaft encoder and a photobeam assembly, the controller accurately locates the positions of containers as they pass through the inspection system and matches collected data to the positions of containers. Accurate matching, improves the detection of defective cans. Additionally, with an accurate determination of a defective can's position, the controller may reliably cause a rejection station to remove the defective can from the manufacturing line.

In general, in another aspect this invention provides a method of operating a manufacturing line for dynamically changing the process control limits for judging internal pressure as a function of slowly varying changes in the upstream container filling process to optimize throughput without permitting the passage of reject containers. In this method, closed containers are passed through a container inspection station, and at this station vibration is induced in a surface of each of the closed containers, sound resulting from this vibration is detected and information is derived representing the detected sound. These steps may be carried out in any of the ways described above. From the information, it is determined whether a frequency component of the information corresponds to a predetermined spectral frequency condition. It is also determined whether an amplitude component of the information corresponds to a predetermined spectral amplitude condition by comparing this amplitude component to a range of values delimited by a lower limit and an upper limit. From a plurality of containers inspected at the container inspection station and judged to be satisfactory by satisfying the predetermined spectral frequency condition and the predetermined spectral amplitude condition, there is accumulated amplitude data for the amplitude components of the containers, and this amplitude data is analyzed to derive therefrom an average value and a deviation. Finally, at least one (and preferably both) of the lower limit and the upper limit are reset in dependence upon the average value and the deviation resulting from the aforementioned analysis.

Implementations of this aspect of the invention may include one or more of the following. The average and the deviation may be calculated as the average and standard deviation of a Gaussian or skew Gaussian distribution and the upper and lower limits may be set to the average plus or minus respectively a predetermined number of standard deviations, desirably not less than 3. The method may include the provision of an absolute lower limit and an absolute upper limit, and the resetting of the limits may be effected so that the lower limit is not set lower than the absolute lower limit, nor is the upper limit set higher than the absolute upper limit. The analysis may include checking that the amplitude data do conform to an assumed standard distribution and that, for example, there is not some abrupt break in the amplitude data part way through the sequence of containers tested which would indicate an abrupt change in the container filling conditions and thus a malfunction in the filling apparatus. Such checking may include deriving an average value and a deviation for a first subset (for example, the first half) of the plurality of containers, deriving an average value and a deviation for a second subset (for example, the second half) of the plurality of containers, where the second subset of containers passed through the container inspection station after the containers in the first subset, calculating the differences between the average values and the deviations for the two subsets, and rejecting the accumulated data if either of these differences exceeds a predetermined value (for example, if either difference exceeds twice that expected by standard statistical group methods). The method may also include the step of checking for modulation distortion in the data and compensating for such modulation distortion if present, as described above.

Other advantages and features will become apparent from the following description, and from the claims.

BRIEF DESCRIPTION OF THE DRAWINGS

The structure, operation, and methodology of the invention, together with other objects and advantages thereof, may best be understood by reading the detailed description in connection with the drawings in which unique reference numerals have been used throughout for each part or feature and wherein.

DETAILED DESCRIPTION

Often, containers being filled and sealed in a manufacturing line are defective due to improper seals or contamination. An improper seal may prevent a container from maintaining a proper vacuum or pressure. Contamination may cause excessive pressure within the container due to outgassing produced by bacteria as the material spoils. To detect improperly pressurized/vacuumed containers, a pulsed magnetic field is imposed on a conductive surface of the container to cause the surface to vibrate, and the acoustic response (i.e., reactant sound) caused by the vibration is analyzed.

The purpose of the analysis is to identify a frequency peak within the reactant sound and determine whether the frequency of that peak falls within predetermined frequency and amplitude ranges of acceptability. Ordinarily, this is a straight forward procedure because the frequency spectrum has a readily identifiable peak occurring at an easily determined frequency. As will be see, however, it is not uncommon for the spectrum to be corrupted by the presence of misleading information introduced into the acoustic signature by distorting modulations that can be present due to the complicated vibratory nature of containers or other components in the measurement system. When this happens, it is necessary to be able to detect the presence of distorting signal modulations before applying the usual procedures for predicting acceptable product. This invention provides the capability for detecting the presence of signal distortion and compensating for it in a manner to be described.

Certain containers, for example, pop top bottles and vacuum packed foil bags, may be improperly pressurized/vacuumed or improperly capped but still produce a reactant sound including a frequency peak within the predetermined frequency range. Analyzing the frequency of the frequency peak alone, therefore, may not allow for the detection of all defective containers.

The amplitude of a frequency peak corresponding to an improperly pressurized/vacuumed container is generally much lower than the amplitude of a frequency peak corresponding to a properly pressurized/vacuumed container. Similarly, the amplitude of a frequency peak corresponding to an improperly capped container is generally much higher than the amplitude of a frequency peak corresponding to a properly capped container. For example, beer bottles that are "double crowned" (i.e., capped twice) may produce a reactant sound including a frequency peak with a very large amplitude. To detect these defective containers, the amplitude of the frequency peak is compared to minimum and maximum amplitude thresholds and the container is rejected if the amplitude falls below the minimum amplitude threshold or exceeds the maximum amplitude threshold.

Figure 1:
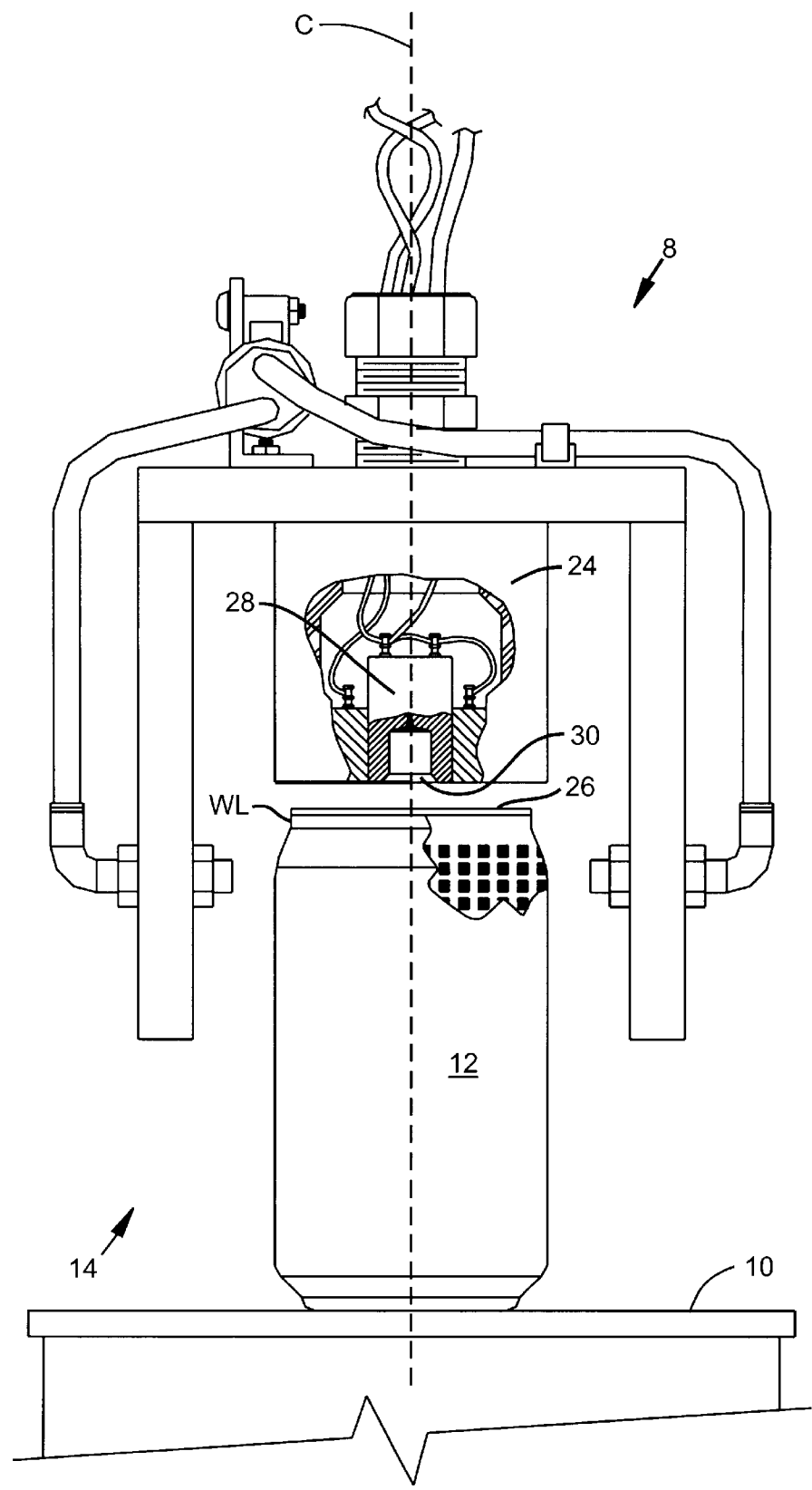
FIG. 1 is a side view partly broken away of a transducer station.
Figure 2:
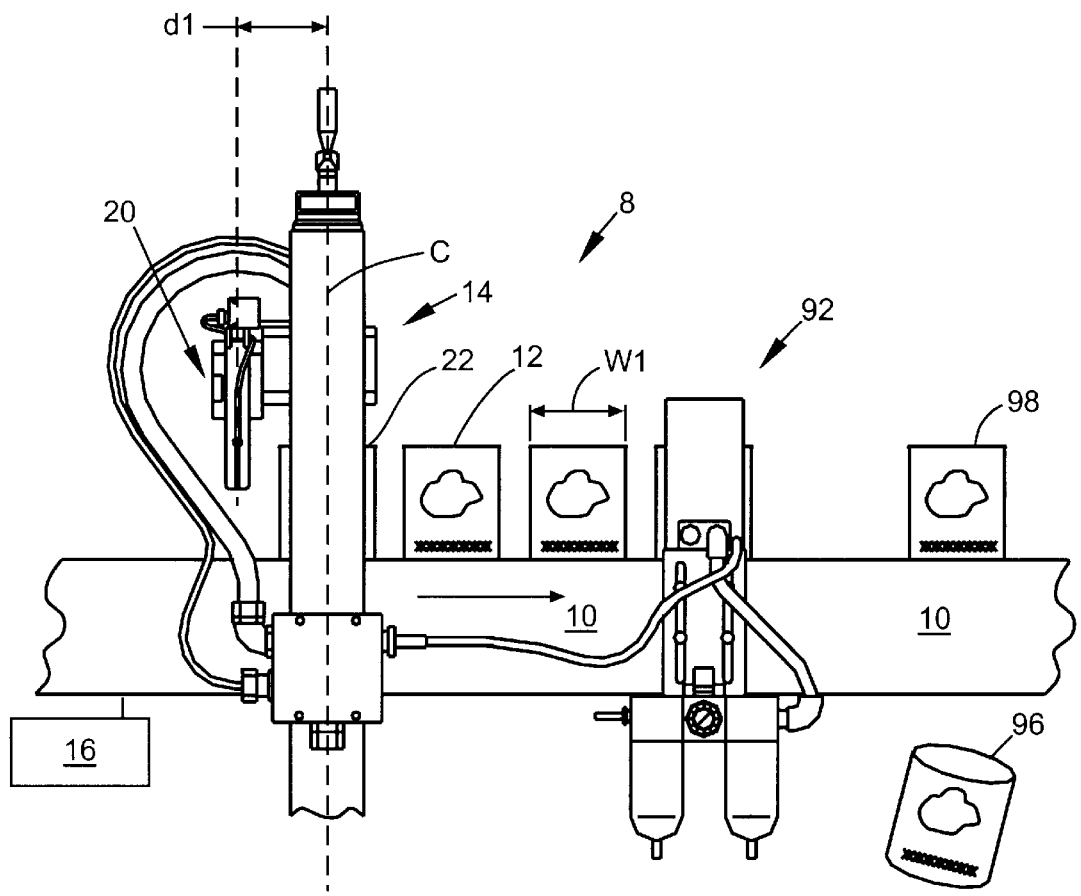
FIG. 2 is a side view of the transducer station of FIG. 1 and a rejecter station.
Figure 3:
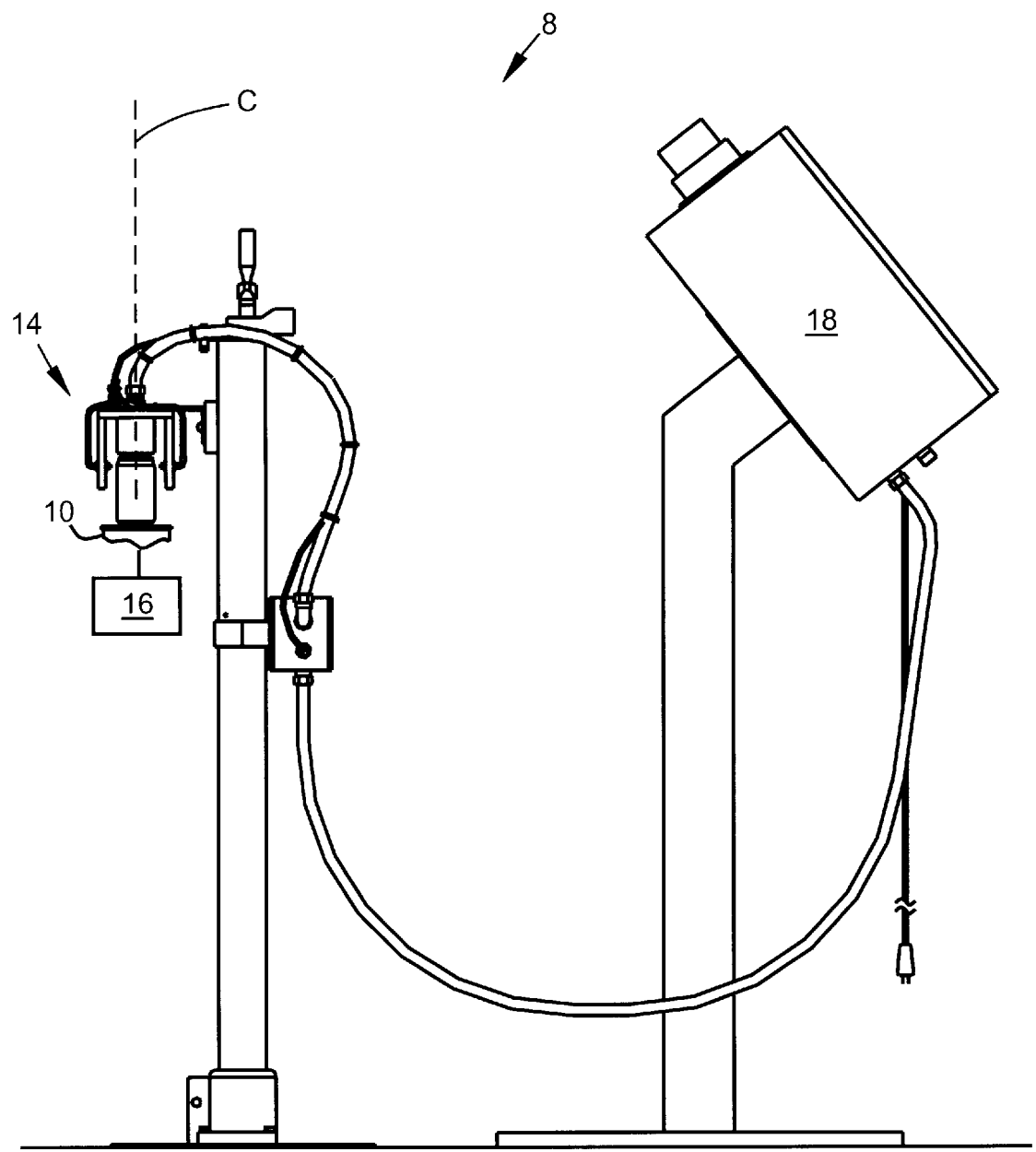
FIG. 3 is an end view of the transducer station of FIG. 1 and a controller.

Referring to FIGS. 1–3, an inspection system 8 includes a conveyor belt 10 that carries closed containers 12 through a transducer station 14 at approximately 3000 containers per minute. A rotary position (shaft) encoder 16 is connected to a drive shaft (not shown) of the conveyor belt and provides a controller 18 with an accurate measurement of the current speed of the conveyor belt. As a container 12 approaches the transducer station 14, a photobeam assembly 20 detects an edge 22 of the container 12 and sends a notification signal to the controller 18. Upon notification, the controller 18 uses the speed of the conveyor belt, the fixed distance, d1, between the photobeam assembly 20 and the transducer station 14, and the width, W1, of the container 12 to calculate the position of the container 12 with respect to the center C of the transducer station 14.

When the container is centered beneath the transducer station 14, the controller 18 sends a signal to the transducer station 14 to cause the station to discharge a capacitor (not shown) through a coil 24. The coil is formed from a closely wound copper tape with Teflon (Registered Trade Mark) backing. The coil 24 is placed in a phenolic form and potted with an epoxy. The discharge produces a pulsed magnetic field which induces eddy currents on a conductive surface 26 of the container 12. The eddy currents generate a back electromagnetic force (the principle of the induction motor) causing the conductive surface 26 to vibrate. The vibration is influenced by the pressure/vacuum within the container 12 and the structure of the container 12 and its contents. A microphone 28, centered within coil 24 senses the acoustic energy (i.e., reactant sound) resulting from the vibration and converts it into a time-varying analog electrical signal which is sent to the controller 18.

The microphone 28 and coil 24 are positioned above a cone 30 to prevent them from being contaminated. Contamination may result from water droplets on container tops and from fluid used to clean the manufacturing line.

The photobeam assembly 20 may be a mini-beam model No. SM312FMHS manufactured by Banner of Minneapolis, Minn. The shaft encoder 16 may be a model No. 62525400021 manufactured by Dynapar of Gurnee, Ill., and the microphone 28 may be a model No. 3140 manufactured by Gentex of Derry, N.H.

Figure 4:
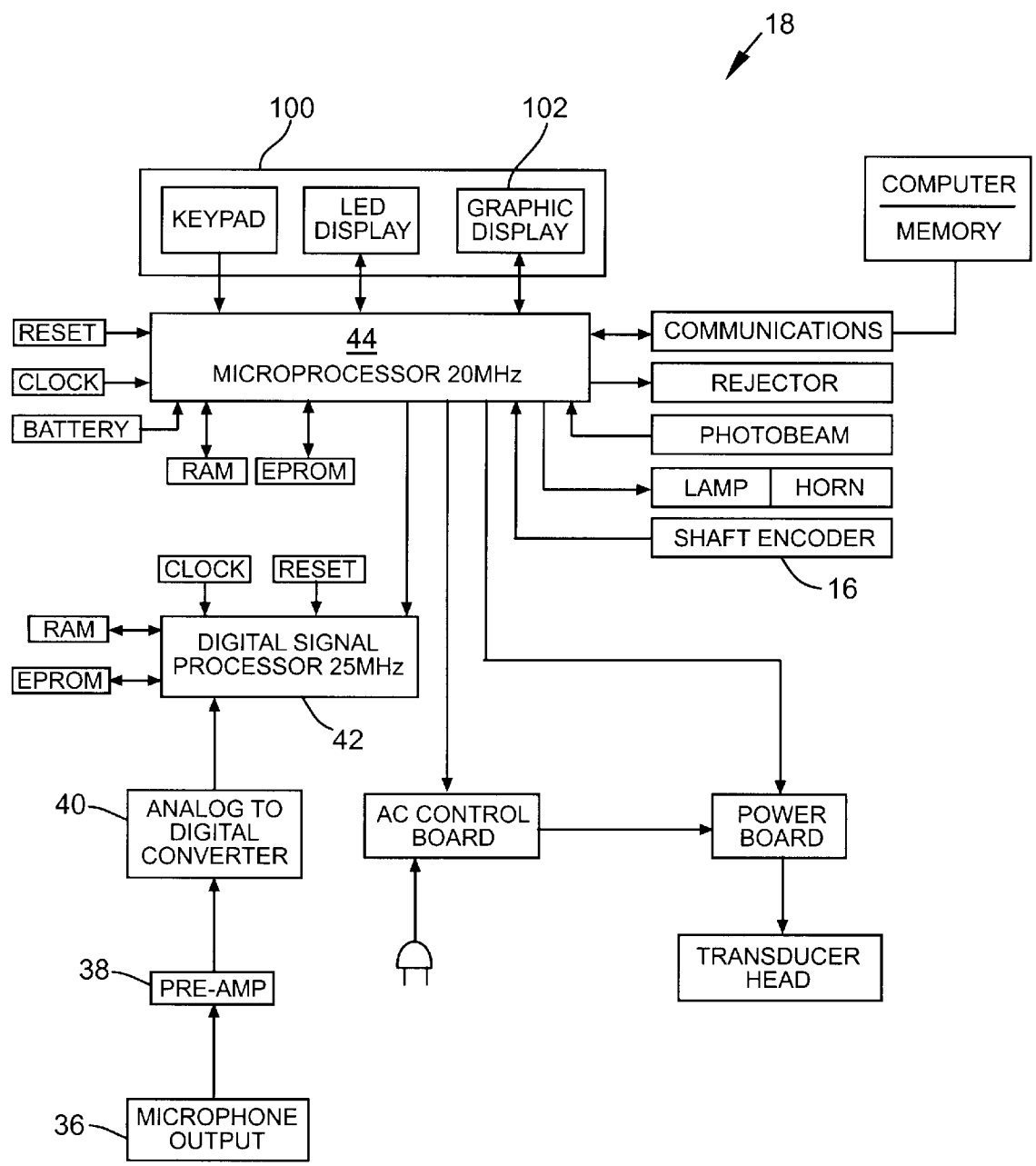
FIG. 4 is a block diagram of the components of the controller of FIG. 3.

Referring to FIG. 4, a microphone input 36 within the controller 18 receives the output signal from the microphone 28 and passes the signal to a preamplifier 38. An analog-to-digital (A/D) converter 40 digitizes the preamplifier's output every 45 microseconds, and a digital signal processor (DSP) 42 stores the A/D converter's digital output. The DSP performs fast Fourier transforms (FFT) on the samples to produce a power spectrum of approximately 512 bins (0–511), with the lower bin numbers corresponding to lower frequencies. The DSP then analyzes the power spectrum to detect for the presence of signal modulation and then determine the frequency and amplitude of the maximum frequency peak within the spectrum. The DSP and other programmable elements of the system are provided with suitable software code to perform the various tasks assigned to them. The sample window on the time domain signal is preferably adjusted to be long enough to capture the desired frequency resolution.

To determine the maximum frequency peak with no distortion present, the DSP 42 compares each bin value within the power spectrum to the next lower and higher bins in frequency. If both the lower and higher bins have values that are less than the value of the bin being considered, then the bin represents a peak. After finding a peak, if the DSP 42 finds another peak within the spectrum, it compares the amplitude of both peaks and stores the frequency and amplitude of the peak with the highest amplitude. Once the DSP 42 has checked the FFT value of each bin within the power spectrum, the frequency and amplitude of the peak with the highest amplitude is sent to a microprocessor 44 for further evaluation. If no peak is found, then the DSP sends an error code to the microprocessor.

If the frequency of the peak is within a predetermined acceptable frequency range and the amplitude of the peak is above a predetermined minimum amplitude and below a predetermined maximum amplitude, then the container 12 is determined to be properly pressurized/vacuumed and properly capped. For instance, referring to FIGS. 5a–5c, frequency domain signals are shown for vacuum-packed pop top bottles containing, for example, fruit juice. The lid 46 (FIGS. 6a–6c) of a pop top bottle 47 has a center portion that is cupped and flexible. When the bottle is properly filled and sealed, the curvature of the cup is concave 48 (FIG. 6c, i.e., in a down position) and the lid maintains a vacuum of approximately 15–25 inches/Hg vacuum within the bottle. Peak frequency 50 (FIG. 5A) at about bin 108 represents the resonant frequency of a properly filled pop top bottle.

The cupped lid of a pop top bottle generally produces approximately the same resonant frequency whether it is in the concave 48 (FIG. 6*c*, down) or convex 52 (FIG. 6*b*, up) position. For example, peak 54 (FIG. 5*b*) represents the resonant frequency of a pop top bottle that is improperly filled but contains a sufficient vacuum to maintain the curvature of the lid in a concave (down) position. The lid of this bottle produces a reactant sound having a frequency peak which is outside a predetermined frequency range 56 of acceptable frequencies. Peak 58 (FIG. 5*c*) represents the reactant sound of a pop top bottle that contains little or no pressure and, thus, the curvature of the lid is in a convex (up) position. In this position, the lid produces a reactant sound having a frequency peak which is within acceptable frequency range 56 and would be accepted if frequency were the only criterion.

To correctly reject both pop top bottles associated with peaks 54 and 58 while accepting the pop top bottle associated with peak 50, the microprocessor analyzes both the frequency and the amplitude of the lid's reactant sound. The bottle associated with peak 50 is accepted because peak 50 is within the predetermined acceptable frequency range 56, above a predetermined minimum amplitude threshold 60, and below a predetermined maximum amplitude threshold 62. The bottles associated with peaks 54 and 58 are rejected because peak 54 is outside acceptable frequency range 56 and peak 58 is below minimum amplitude threshold 60.

Figure 8:
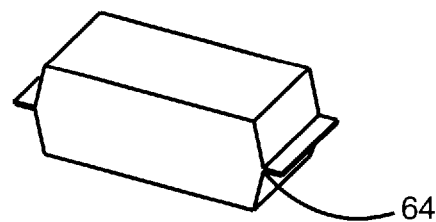
FIG. 8 is a perspective view of a vacuum packed foil bag.
Figure 7A:
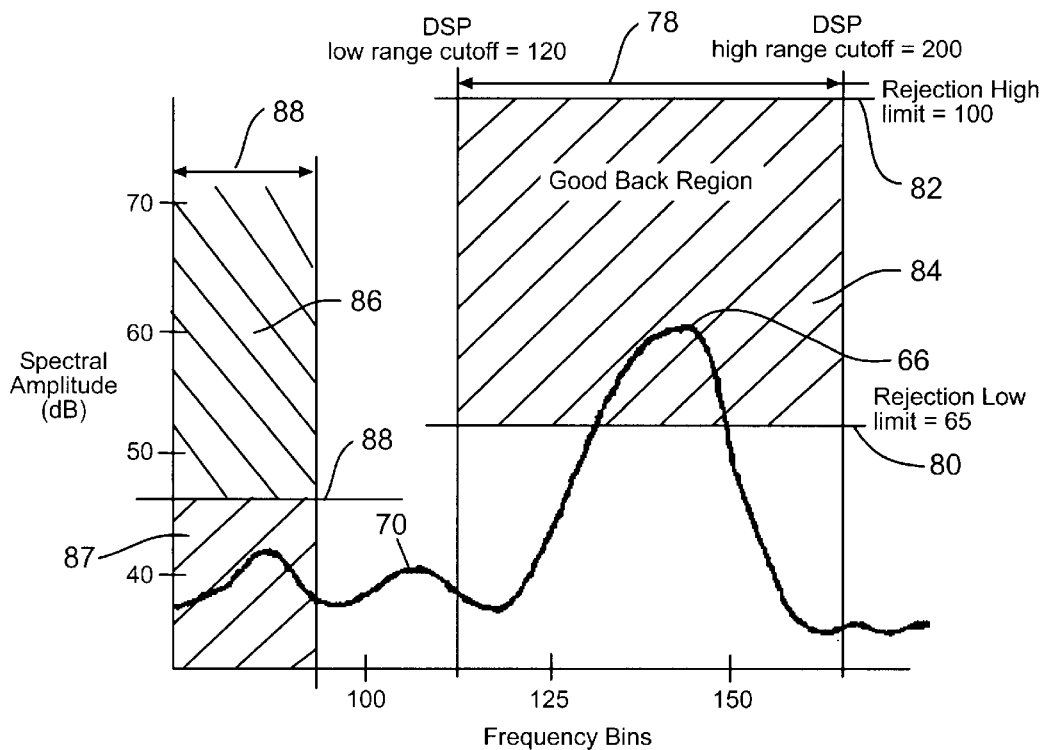
FIGS. 7a and 7b are frequency domain graphs of coffee brick acoustic responses for different internal vacuums.
Figure 7B:
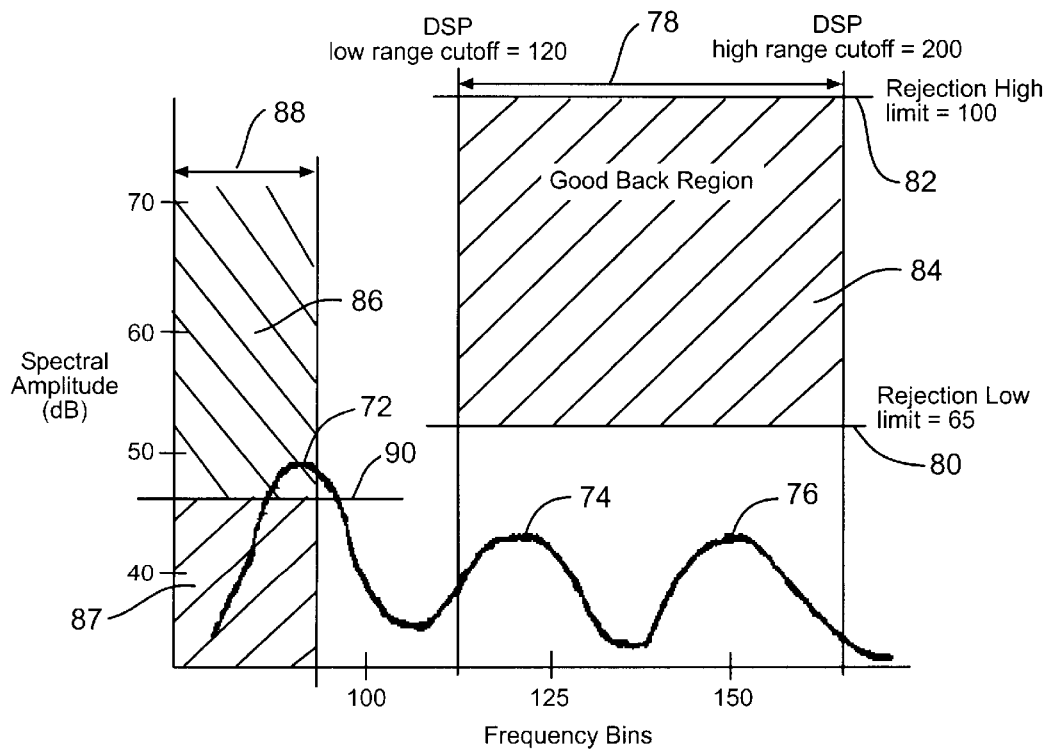

Referring to FIGS. 7*a* and 7*b*, power spectrums are shown for vacuum-packed bricks 64 (FIG. 8, e.g., coffee grounds vacuum packed in a rectangular foil bag). The package containing the coffee grounds is flexible and when the package is properly filled and sealed, it provides a hard surface and maintains a vacuum of approximately 100 mbar. Maximum peak 66, at about bin 130, represents the resonant frequency of a properly filled coffee brick.

Because the package is flexible, it generally produces multiple frequency peaks 66, 68, and 70. Peaks 72, 74, and 76 represent the reactant sound of an improperly filled (i.e., soft) brick. The controller correctly rejects the brick associated with peaks 72, 74, and 76 and correctly accepts the brick associated with peaks 66, 68, and 70 again by analyzing both the frequency and amplitude of the maximum frequency peak of the package's reactant sound to determine whether the brick is properly filled. The brick associated with peaks 66, 68, and 70 is accepted because maximum peak 66 is both within a predetermined acceptable frequency range 78, above a predetermined maximum amplitude threshold 82. The brick associated with peaks 72, 74, and 76 is rejected because 72 is outside the acceptable frequency range and peaks 74 and 76, which are within the acceptable frequency range, are below the minimum amplitude threshold 80.

Improperly filled bricks generally resonate at lower frequencies, e.g., peak 72, than properly filled bricks, e.g., peak 66. Therefore, instead of determining which bricks are properly sealed by looking for a frequency response within a good brick (container) region 84, the controller can determine which bricks are bad by looking for a frequency peak within a bad brick (container) region 86 above a good brick (container) region 87. For example, within a lower predetermined frequency range 88, a properly filled brick will not produce a reactant sound that includes a threshold 90. Thus, the microprocessor can reject every brick that produces a reactant sound having a frequency peak that is above the minimum amplitude threshold 90 within the frequency range.

Referring back to FIG. 2, after determining that a container is defective, the controller sends a signal to a rejecter station 92 to cause the rejecter station to remove the defective container from the manufacturing line. The rejecter may be an actuator 94 including a position with a bumper (not shown) positioned next to the conveyor belt to push improperly sealed containers 96 off the conveyor. Properly sealed containers 98 remain on the conveyor. The piston timing is accurately determined as a specific number of shaft encoder pulses after the container leaves the photobeam. Because the encoder accurately measures the speed of the conveyor belt, rejecter errors due to changes in conveyor belt speed are minimized.

Referring again to FIG. 3, an operator may set the predetermined frequency range and the minimum and maximum amplitudes (i.e., set-up parameters) through a console 100 (FIG. 4) on controller 18. These values may be empirically determined by passing a series of properly and improperly pressurized/vacuumed containers through the inspection system and observing the resulting power spectrums corresponding to each container on a graphic display 102. The graphic display contains a plot of the power spectrum including the maximum peak's bin number and amplitude (dB). The set-up parameters may then be stored within the controller. After a variety of types of containers have been tested and their set-up parameters stored, operators may initialize the inspection system for each container type by selecting from a list of container types corresponding to previously stored set-up parameters.

Figure 5A:
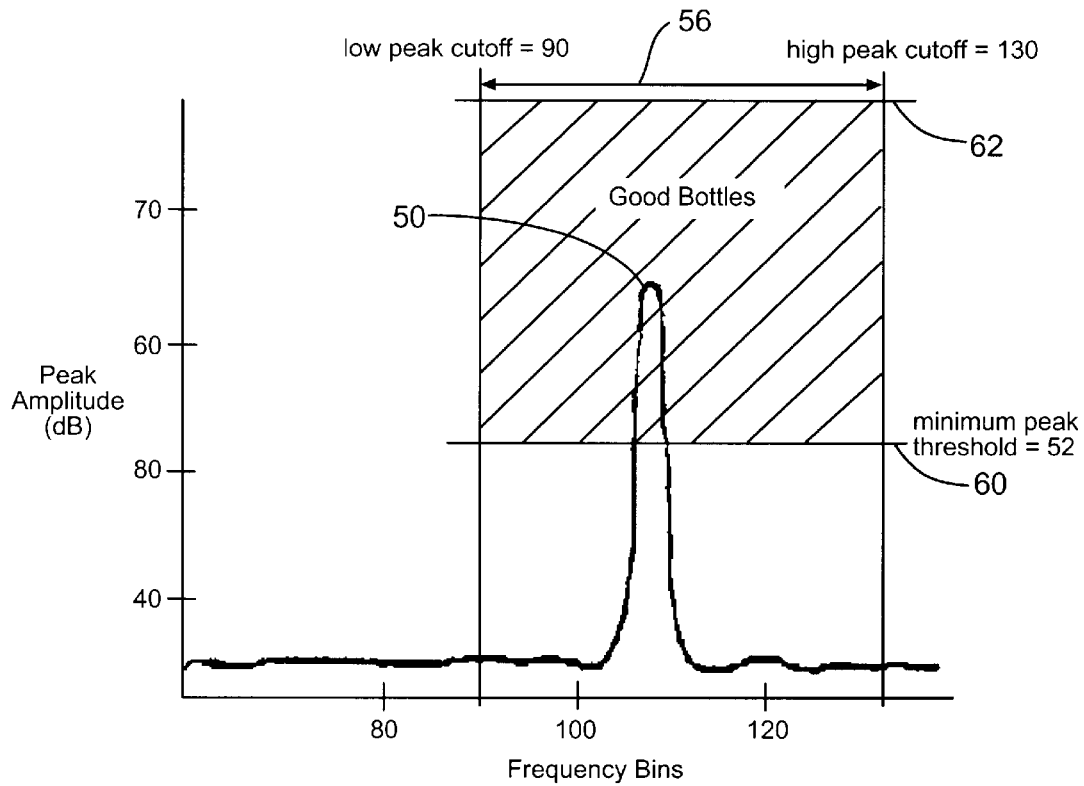
FIGS. 5a–5c are frequency domain graphs of pop top bottle acoustic responses for different internal vacuums.
Figure 5B:
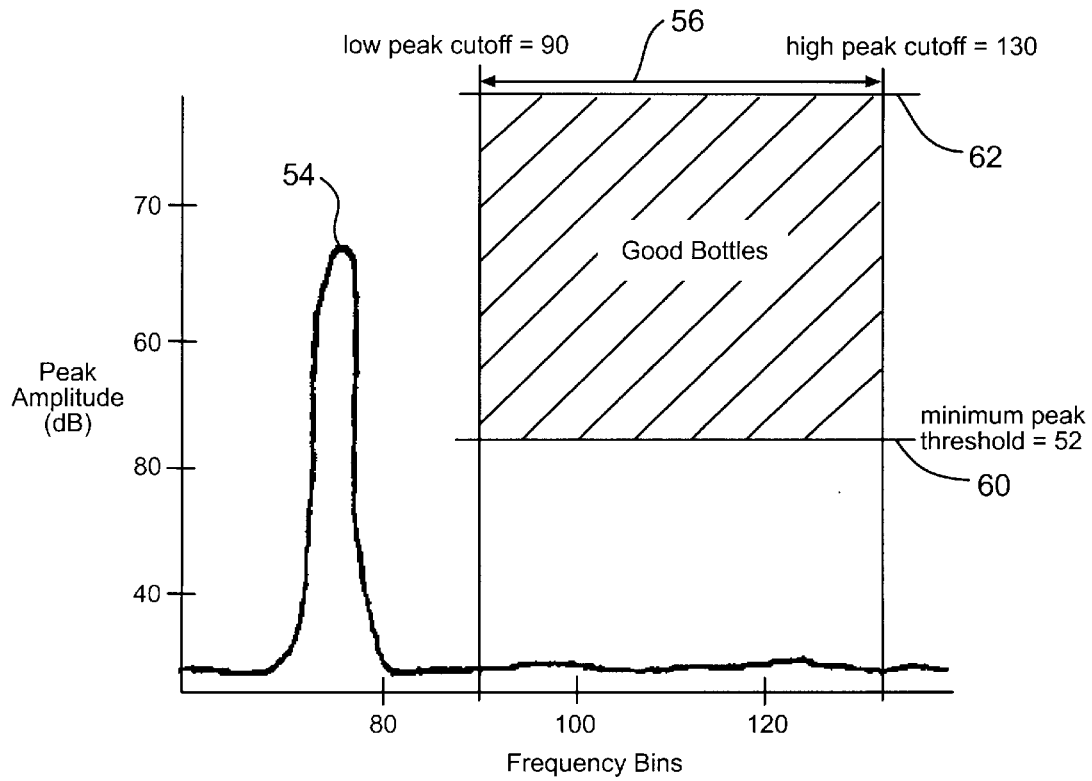
Figure 5C:
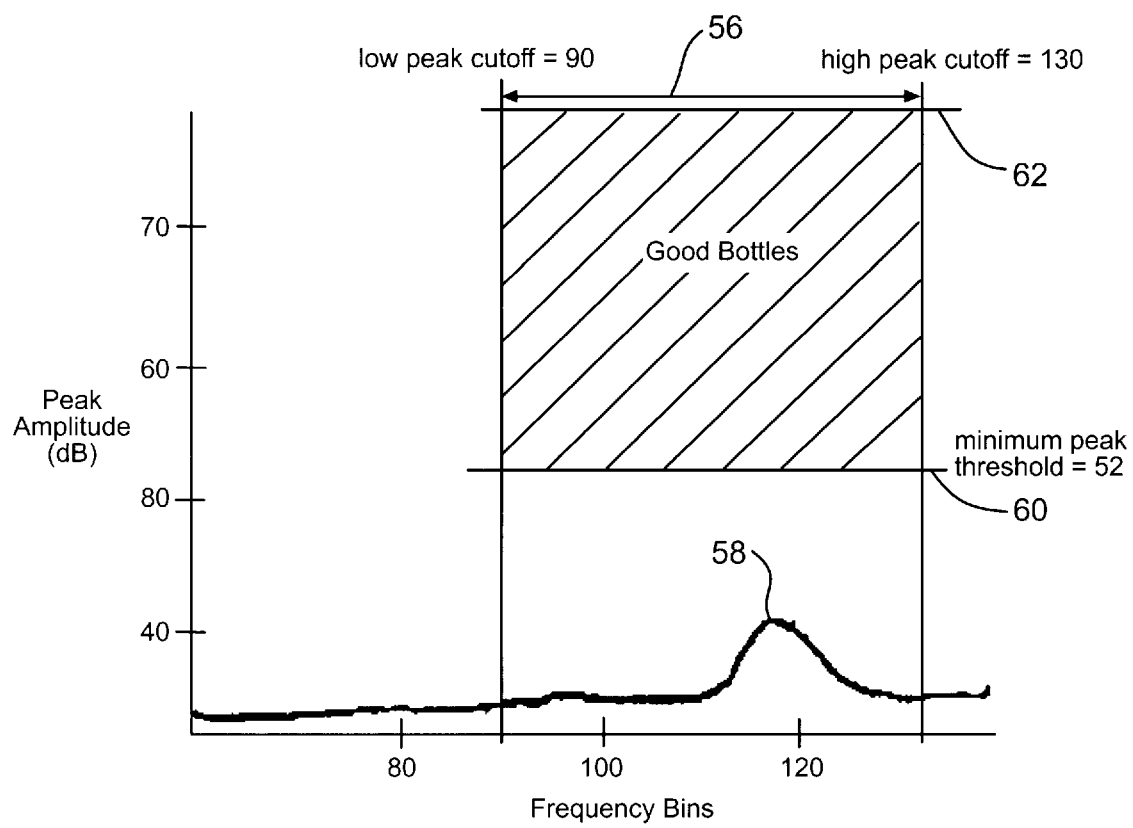
Figure 6A:
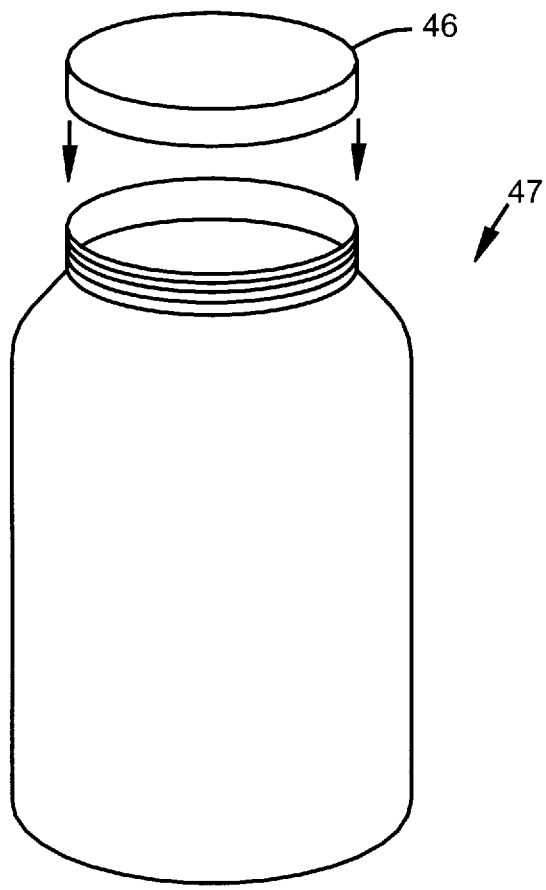
FIG. 6a is a perspective view of a pop top bottle.
Figure 6B:
FIGS. 6b and 6c are cross-sectional side views of a pop top bottle lid.
Figure 6C:
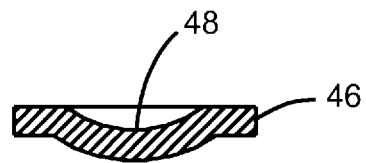
Figure 9:
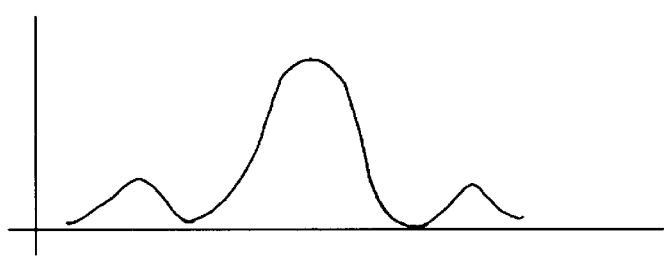
FIG. 9 is a diagrammatic graph illustrating the distribution of peak responses as a function of frequency for a population of containers in which signal distortion is present.

It will be appreciated that the peak (resonant) frequency of properly filled container, such as that of the peak 50 shown in FIG. 5*a*, is subject to normal statistical variation, so that if measures this peak frequency for a large number of properly filled containers and prepares a histogram of the number of containers versus peak frequency, if no modulating distortion is present in the data, this histogram will normally resemble a Gaussian curve, as shown in the central portion of FIG. 9. However, when modulating distortion is present in a container's acoustic spectrum, the histogram is altered to provide a population distribution as shown in FIG. 9, containing two side lobes. These side lobes actually contain acceptable containers, but these acceptable container may be identified as rejects if the modulations are not accounted for. For example, if FIG. 9 were derived from the same containers as those used to produce FIG. 5*a*, the frequency difference between the central lobe of FIG. 9 and the left-hand lobe can easily be sufficient that many containers in the left-hand lobe might have their peak frequencies 50 (FIG. 5*a*) shifted so far towards lower frequencies that the peak would lie below the low peak cutoff shown in that Figure, and consequently the containers would be rejected as failing to satisfy the spectral frequency condition.

When the reactant acoustic signal contains modulating distortion, the distortion must first be detected and, if found, the modulating distortion may be removed from the spectrum or the fact of its presence used in interpreting the power spectrum so that the modulating distortion is compensated. The procedure for detection and removal or compensation of the modulating distortion should be applied before the usual methodology for testing amplitude and frequency components of the signal discussed above.

Determining if modulating distortion is present in a signal may be done in either the time domain or the frequency domain. While the frequency domain approach is preferred in practice, the time domain approach will first be described to illustrate the nature of the problem.

Figure 10:
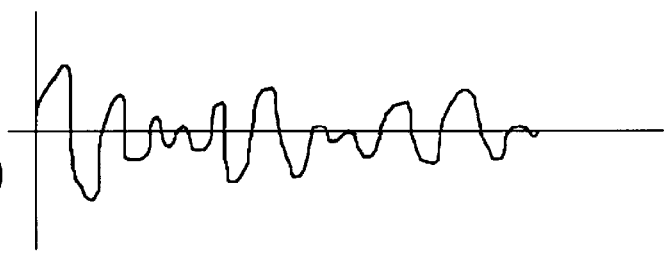
FIG. 10 is a diagrammatic representation of an acoustic container time domain signal in which distorting modulation is present.
Figure 11:
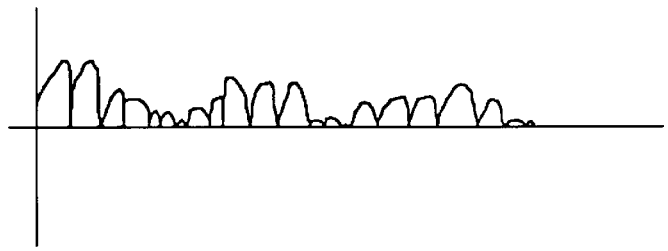
FIG. 11 is a diagrammatic representation of the signal of FIG. 10 in rectified form.
Figure 12:
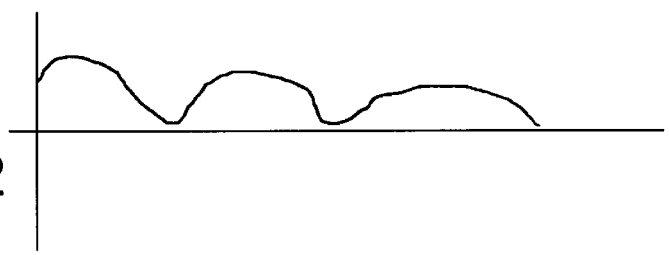
FIG. 12 is a diagrammatic representation of the modulation signal present in FIG. 10.
Figure 13:
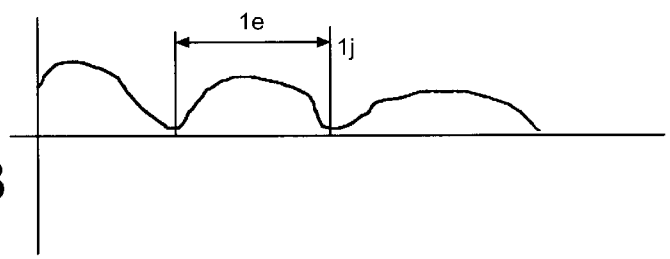
FIG. 13 is a diagrammatic representation of the signal of FIG. 12 showing the period of the modulating signal.
Figure 14:
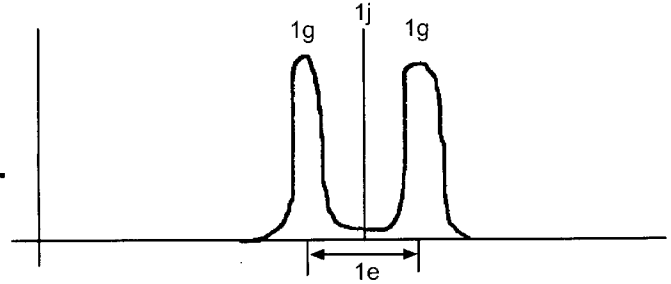
FIG. 14 is a diagrammatic representation of the splitting effect that the presence of a modulating component can have on the fundamental frequency response of a container.

If done in the time domain, one preferred method can be as follows. Referring now to FIG. 10 there is shown an acoustic signal in the time domain that contains distorting modulation. The method for dealing with this modulation is to first rectify the signal of FIG. 10 so that it appears as in FIG. 11. The rectified signal of FIG. 11 may be processed by applying a lowpass filter to generate the time varying signal of the modulation as shown in FIG. 12, although this step is not essential. The signal of FIG. 12 is then checked for any periodic waveforms. This is done by checking the modulation waveform for the existence of minima. A possible modulation frequency (1e) is then determined by the separation of the minima in the time domain as indicated in FIG. 13 to the corresponding frequency. This possible modulation frequency is used to check the frequency spectrum as shown in FIG. 14 for any possible frequency peaks (1g) that are separated by the modulation frequency (1e). If the modulation is present in the frequency spectrum of FIG. 14 as indicated by two peaks (1g) separated by the modulation frequency(1e), the modulation distortion can be compensated for by replacing the two frequency peaks (1g) with a single peak lying at the actual undistorted frequency (1i) half way between the two frequency peaks. (Note that in practice it may not be possible to place the single peak exactly half way between the two frequency peaks; FIGS. 9–14 essentially assume a continuous variation in frequency, whereas, as discussed above with reference to FIGS. 5a, 5b, 5c, 7a and 7b, in practice the frequency spectrum is analyzed in a finite number of bins. If, for example, in practice the two peaks in FIG. 14 were at bin 100 and bin 111, one would need to replace them with a single peak at either bin 105 or bin 106. However, provided the single peak is placed substantially at the frequency half way between the two peaks, any minor deviation due to the finite number of bins does not significantly affect the results.) Desirably, the amplitude of the single peak is set equal to that of the larger of the two original peaks. Because a power spectrum is being used, it is permissible to take the larger of the two peaks since the difference between the two peaks in db level is acceptably small compared with the differences in level at which rejection occurs.

Alternatively, and preferably, in testing for the presence of modulating distortion, one can proceed directly to the frequency power spectrum of FIG. 14 and analyze it for the presence of two peaks of substantially equal amplitude separated by a frequency difference no greater more than a predetermined amount. If this condition is satisfied, that is, if the peaks fall within the predetermined frequency interval, modulating distortion is judged to be present, and the pair of peaks is replaced by a single peak in the manner previously described, this single peak having a frequency half way between frequencies of the pair of peaks occur, and an amplitude equal to that of the larger of the pair of peaks. The frequency and amplitude of this single new peak are then used as before to determine if the container response falls within the desired frequency range and within the desired amplitude range.

As already discussed, another aspect of the invention provides for automatic adjustment (resetting) of acceptable amplitude limits by assessing contemporaneous process capability and setting floating amplitude limits to optimize acceptable product. Since the upstream process for filling containers changes slowly in comparison to catastrophic failures, one can set floating amplitude limits so long as they do not exceed predetermined absolute upper and lower limits considered to represent failure levels. This adjustment or resetting is done by sampling a sequence of containers judged to be acceptable by the frequency/amplitude analysis already described and determining the distribution of peak amplitudes over some time interval. A sample interval corresponding to 128 containers has been found acceptable for this purpose. Here, the distribution of amplitudes is monitored (typically a normal distribution), an average and a deviation for this distribution is calculated and the upper and lower limits are reset to the average plus and minus respectively a predetermined number of deviations; in some cases, it may be desirable to reset only one of the upper and lower limits. Typically, the 3σ (i.e., three times the standard deviation) limits for the 128 containers are used to automatically update the upper and lower limits on amplitude for the next 128 containers, although other multiples of σ-limits may be used. In this way, the amplitude limits of acceptability can vary in accordance with slowly varying process conditions with the result that less product is rejected as the process slowly changes. However, as already indicated, to guard against the process dramatically changing (which probably indicates a malfunction in the filling apparatus), this screening technique can be provided with safeguards in the form of commands to ignore the adjustment of the floating point values and a signal that the process is out of control. For example, the process may include analysis to check that the amplitude data do conform to an assumed standard distribution; one possible technique for such analysis is to calculate an average and a deviation for two subsets of containers, for example the first and second halves of the 128 containers, calculate the differences two the two averages and the two deviations and reject the data for all 128 containers (and preferably generate an alarm) if either of these differences exceeds a predetermined value. Appropriate methods for setting this predetermined value will be apparent to those skilled in statistical analysis.

While the invention has been described with reference to particular embodiments thereof, those skilled in the art will be able to make various modifications to the described embodiments of the invention without departing from its true spirit and scope.

I claim:

1. A method for analyzing the internal pressure of containers, said method comprising the steps of:

inducing vibration in a surface of a closed container;

detecting sound resulting from the vibration;

deriving original information representing the detected sound;

testing said original information to determine whether a modulating distortion is present in said original information, and if so compensating for the effects of said modulating distortion, thereby producing demodulated information;

determining whether a frequency component of (a) said original information, if no modulating distortion has been found therein, or (b) said demodulated information, if modulating distortion has been found in the original information, corresponds to a predetermined spectral frequency condition; and determining whether an amplitude component of (a) said original information, if no modulating distortion has been found therein, or (b) said demodulated information, if modulating distortion has been found in the original information, corresponds to a predetermined spectral amplitude condition.

2. A method according to claim 1 wherein said testing of said original information is effected by:

rectifying said original information to produce rectified information;

testing said rectified information for the presence of periodic minima, and if periodic minima are detected, measuring the period between successive minima, and converting this period to a possible modulation frequency;

deriving a frequency spectrum of said original information;

testing said frequency spectrum for the presence of a pair of peaks separated by a frequency difference substantially equal to said possible modulation frequency.

3. A method according to claim 2 wherein said rectified information is lowpass filtered before being tested for the presence of periodic minima.

4. A method according to claim 2 wherein said compensating for the effects of said modulating distortion is effected by replacing said pair of peaks in said frequency spectrum with a single peak lying substantially at the frequency halfway between said pair of peaks.

5. A method according to claim 4 wherein the amplitude of said single peak is made substantially equal to the larger of the amplitudes of said pair of peaks.

6. A method according to claim 1 wherein said testing of said original information is effected by:

deriving a frequency spectrum of said original information;

testing said frequency spectrum for the presence of a pair of peaks of substantially equal amplitude separated by a frequency difference less than a predetermined value.

7. A method according to claim 6 wherein said compensating for the effects of said modulating distortion is effected by replacing said pair of peaks in said frequency spectrum with a single peak lying substantially at the frequency halfway between said pair of peaks.

8. A method according to claim 7 wherein the amplitude of said single peak is made substantially equal to the larger of the amplitudes of said pair of peaks.

9. A method according to claim 1 wherein the surface is at least partially conductive and said inducing includes imposing a magnetic field on the surface.

10. A method according to claim 1 wherein the predetermined spectral frequency condition corresponds to a range of acceptable values.

11. A method according to claim 1 wherein the predetermined spectral amplitude condition corresponds to a range of acceptable values.

12. A method according to claim 1 wherein the detected sound is used to determine whether the closed container contains a pressure level within a predetermined range of pressure levels.

13. A method for analyzing the internal pressure of containers, said method comprising the steps of:

inducing vibration in a surface of a closed container by imposing a magnetic field on the surface;

detecting sound resulting from the vibration;

deriving original information representing the detected sound;

testing said original information to determine whether a modulating distortion is present in said original information, and if so compensating for the effects of said modulating distortion, thereby producing demodulated information;

determining whether a frequency component of (a) said original information, if no modulating distortion has been found therein, or (b) said demodulated information, if modulating distortion has been found in the original information, corresponds to a predetermined frequency condition, wherein the predetermined frequency condition corresponds to a range of acceptable frequencies, including comparing the information to the range of acceptable frequencies; and determining whether an amplitude component of (a) said original information, if no modulating distortion has been found therein, or (b) said demodulated information, if modulating distortion has been found in the original information, corresponds to a predetermined amplitude condition, wherein the predetermined amplitude condition corresponds to a minimum or a maximum amplitude threshold, including comparing the information to the amplitude threshold.

14. A method of operating a manufacturing line, the method comprising:

passing closed containers through a container inspection system, and at the container inspection system inducing vibration in a surface of each of the closed containers;

detecting sound resulting from the vibration;

deriving original information representing the detected sound;

testing said original information to determine whether a modulating distortion is present in said original information, and if so compensating for the effects of said modulating distortion, thereby producing demodulated information;

determining whether a frequency component of (a) said original information, if no modulating distortion has been found therein, or (b) said demodulated information, if modulating distortion has been found in the original information, corresponds to a predetermined spectral frequency condition; and determining whether an amplitude component of (a) said original information, if no modulating distortion has been found therein, or (b) said demodulated information, if modulating distortion has been found in the original information, corresponds to a predetermined spectral amplitude condition.

15. A method according to claim 14 further comprising rejecting and accepting containers based on the results of the determining step.

16. A method according to claim 15 including rejecting containers for which said information used in said determination shows spectral frequency peaks that are outside a range of acceptable frequencies, and also rejecting containers for which said information shows spectral frequency peaks that are within a range of acceptable frequencies but which have amplitudes below a minimum amplitude threshold or above a maximum amplitude threshold.

17. A method of operating a manufacturing line, the method comprising:

passing closed containers through a container inspection station, and at the container inspection station inducing vibration in a surface of each of the closed containers;

detecting sound resulting from the vibration;

deriving information representing the detected sound;

determining whether a frequency component of said information corresponds to a predetermined spectral frequency condition; and determining whether an amplitude component of said information corresponds to a predetermined spectral amplitude condition by comparing said amplitude component to a range of acceptable values delimited by a lower limit and an upper limit;

accumulating, from a plurality of containers inspected at the container inspection station and judged to be satisfactory by satisfying said predetermined spectral frequency condition and said predetermined spectral amplitude condition, amplitude data for the amplitude components of said containers;

analyzing said amplitude data to derive an average value and a deviation therefrom; and resetting at least one of said lower limit and said upper limit in dependence upon said average value and said deviation.

18. A method according to claim 17 wherein both said lower limit and said upper limit are reset in dependence upon said average value and said deviation.

19. A method according to claim 18 wherein said average and said deviation are calculated as the average and standard deviation of a Gaussian or skew Gaussian distribution and said upper and lower limits are set to the average plus and minus respectively a predetermined number of standard deviations.

20. A method according to claim 19 wherein said predetermined number of standard deviations is not less than 3.

21. A method according to claim 17 wherein there are predetermined an absolute lower limit and an absolute upper limit, and said resetting is effected so that the lower limit is not set lower than the absolute lower limit, nor is the upper limit set higher than said absolute upper limit.

22. A method according to claim 17 wherein said analysis includes checking that the amplitude data do conform to an assumed standard distribution.

23. A method according to claim 22 wherein said checking includes:

deriving an average value and a deviation for a first subset of said plurality of containers;

deriving an average value and a deviation for a second subset of said plurality of containers, where said second subset of containers passed through the container inspection system after the containers in the first subset;

calculating the differences between the average values and the deviations for the two subsets; and rejecting said accumulated data if either of said differences exceeds a predetermined value.

24. A method according to claim 23 wherein said information representing the detected sound is tested to determine whether a modulating distortion is present in said information, and if so compensating for the effects of said modulating distortion, thereby producing demodulated information;

and wherein said determinations as to whether a frequency component of said information corresponds to a predetermined spectral frequency condition; and whether an amplitude component of said information corresponds to a predetermined spectral amplitude condition are effected using (a) said information representing the detected sound, if no modulating distortion has been found therein, or (b) said demodulated information, if modulating distortion has been found in the original information representing the detected sound.

25. A method according to claim 24 wherein said testing of said original information derived from the detected sound is effected by:

rectifying said original information to produce rectified information;

testing said rectified information for the presence of periodic minima, and if periodic minima are detected, measuring the period between successive minima, and converting this period to a possible modulation frequency;

deriving a frequency spectrum of said original information;

testing said frequency spectrum for the presence of a pair of peaks separated by a frequency difference substantially equal to said possible modulation frequency.

26. A method according to claim 25 wherein said rectified information is lowpass filtered before being tested for the presence of periodic minima.

27. A method according to claim 25 wherein said compensating for the effects of said modulating distortion is effected by replacing said pair of peaks in said frequency spectrum with a single peak lying substantially at the frequency halfway between said pair of peaks.

28. A method according to claim 27 wherein the amplitude of said single peak is made substantially equal to the larger of the amplitudes of said pair of peaks.

29. A method according to claim 25 wherein said testing of said original information derived from the detected sound is effected by:

deriving a frequency spectrum of said original information;

testing said frequency spectrum for the presence of a pair of peaks of substantially equal amplitude separated by a frequency difference less than a predetermined value.

30. A method according to claim 29 wherein said compensating for the effects of said modulating distortion is effected by replacing said pair of peaks in said frequency spectrum with a single peak lying substantially at the frequency halfway between said pair of peaks.

31. A method according to claim 30 wherein the amplitude of said single peak is made substantially equal to the larger of the amplitudes of said pair of peaks.

32. Apparatus for analyzing the internal pressure of a closed container, the apparatus comprising:

vibration means for inducing vibration in a surface of the closed container;

sound detection means for detecting sound resulting from the vibration;

information derivation means for deriving original information representing the detected sound; and data processing means arranged to:

(a) test said original information to determine whether a modulating distortion is present in said original information, and if so to compensate for the effects of said modulating distortion, thereby producing demodulated information;

(b) determine whether a frequency component of (a) said original information, if no modulating distortion has been found therein, or (b) said demodulated information, if modulating distortion has been found in the original information, corresponds to a predetermined spectral frequency condition;

(c) determine whether an amplitude component of (a) said original information, if no modulating distortion has been found therein, or (b) said demodulated information, if modulating distortion has been found in the original information, corresponds to a predetermined spectral amplitude condition; and (d) produce a first output signal if said frequency component and said amplitude component correspond to said predetermined spectral frequency and amplitude condition respectively, and a second output signal if said frequency component fails to satisfy said predetermined spectral frequency condition or said amplitude component fails to satisfy said predetermined spectral amplitude condition.

33. Apparatus according to claim 32 wherein said data processing means is arranged to test said original information by:

rectifying said original information to produce rectified information;

testing said rectified information for the presence of periodic minima, and if periodic minima are detected, measuring the period between successive minima, and converting this period to a possible modulation frequency;

deriving a frequency spectrum of said original information;

testing said frequency spectrum for the presence of a pair of peaks separated by a frequency difference substantially equal to said possible modulation frequency.

34. Apparatus according to claim 33 wherein said data processing means is arranged to lowpass filter said rectified information before testing said rectified information for the presence of periodic minima.

35. Apparatus according to claim 33 wherein said data processing means is arranged to compensate for the effects of said modulating distortion by replacing said pair of peaks in said frequency spectrum with a single peak lying substantially at the frequency halfway between said pair of peaks.

36. Apparatus according to claim 35 wherein said data processing means sets the amplitude of said single peak substantially equal to the larger of the amplitudes of said pair of peaks.

37. Apparatus according to claim 32 wherein said data processing means is arranged to test said original information by:

deriving a frequency spectrum of said original information;

testing said frequency spectrum for the presence of a pair of peaks of substantially equal amplitude separated by a frequency difference less than a predetermined value.

38. Apparatus according to claim 37 wherein said data processing means is arranged to compensate for the effects of said modulating distortion by replacing said pair of peaks in said frequency spectrum with a single peak lying substantially at the frequency halfway between said pair of peaks.

39. Apparatus according to claim 38 wherein said data processing means sets the amplitude of said single peak substantially equal to the larger of the amplitudes of said pair of peaks.

40. A manufacturing line having a container inspection station and transport means for moving closed containers through the container inspection station, the container inspection station comprising:

vibration means for inducing vibration in a surface of a closed container at the container inspection station; and sound detection means for detecting sound resulting from the vibration, wherein the manufacturing line further comprises:

information derivation means for deriving information representing the detected sound; and data processing means arranged to:

(a) determine whether a frequency component of said information corresponds to a predetermined spectral frequency condition; and (b) determine whether an amplitude component of said information corresponds to a predetermined spectral amplitude condition by comparing said amplitude component to a range of acceptable values delimited by a lower limit and an upper limit;

(c) accumulate, from a plurality of containers judged to be satisfactory by satisfying said predetermined spectral frequency condition and said predetermined spectral amplitude condition, amplitude data for the amplitude components of said containers;

(d) analyze said amplitude data to derive an average value and a deviation therefrom; and (e) reset at least one of said lower limit and said upper limit in dependence upon said average value and said deviation.

41. Apparatus according to claim 40 wherein the data processing means is arranged to reset both said lower limit and said upper limit in dependence upon said average value and said deviation.

42. Apparatus according to claim 41 wherein the data processing means is arranged to calculate the average and standard deviation of a Gaussian or skew Gaussian distribution and to reset said upper and lower limits to the average plus and minus respectively a predetermined number of standard deviations.

43. Apparatus according to claim 40 wherein the data processing means is arranged to check that the amplitude data do conform to an assumed standard distribution.

44. Apparatus according to claim 43 wherein the data processing means effects said checking by:

deriving an average value and a deviation for a first subset of said plurality of containers;

deriving an average value and a deviation for a second subset of said plurality of containers, where said second subset of containers passed through the container inspection system after the containers in the first subset;

calculating the differences between the average values and the deviations for the two subsets; and rejecting said accumulated data if either of said differences exceeds a predetermined value.

45. Apparatus according to claim 40 wherein said data processing means is arranged to test said information representing the detected sound to determine whether a modulating distortion is present in said information, and if so to compensate for the effects of said modulating distortion, thereby producing demodulated information, and wherein the determination of whether a frequency component corresponds to a predetermined spectral frequency condition and whether an amplitude component corresponds to a predetermined spectral amplitude condition are carried out the information representing the detected sound, if no modulating distortion has been found therein, but are carried out on said demodulated information, if modulating distortion has been found.

* * * * *